United States Patent

Parkhurst et al.

Patent Number: 5,412,372
Date of Patent: May 2, 1995

[54] ARTICLE DISPENSER FOR MONITORING DISPENSING TIMES

[75] Inventors: Larry E. Parkhurst, Boulder, Colo.; Edward M. Aten, Clarkson Valley, Mo.

[73] Assignee: Medical Microsystems, Inc., Boulder, Colo.

[21] Appl. No.: 948,208

[22] Filed: Sep. 21, 1992

[51] Int. Cl.[6] ............................................. G08B 21/00
[52] U.S. Cl. ............................. 340/568; 221/2; 221/15; 340/540; 368/10
[58] Field of Search ............... 340/568, 540; 368/10; 221/2, 15, 197

[56] References Cited

U.S. PATENT DOCUMENTS

| | | | |
|---|---|---|---|
| 4,526,474 | 7/1985 | Simon | 368/10 |
| 4,572,403 | 2/1986 | Benaroya | 221/197 |
| 4,616,316 | 10/1986 | Hanpeter et al. | 340/303 |
| 4,617,557 | 10/1986 | Gordon | 340/568 |
| 4,660,991 | 4/1987 | Simon | 368/10 |
| 4,717,042 | 1/1988 | McLaughlin | 221/197 |
| 4,939,705 | 7/1990 | Hamilton et al. | 368/108 |
| 4,971,221 | 11/1990 | Urquhart et al. | 221/2 |
| 5,181,189 | 1/1993 | Hafner | 368/10 |

Primary Examiner—Glen Swann
Attorney, Agent, or Firm—Beaton & Swanson

[57] ABSTRACT

A portable medication dispenser aids and monitors regimen-conforming use of medications provided in standard as-marketed blister packages. A standard blister package and a separate, disposable sensor sheet are simply and easily loaded into a compact housing containing supervisory electronics, visual indicators, and an audible alarm. The sensor sheet consists of electrical or optical sensing regions corresponding to each individual compartment of the blister package. A compliant, electrically conductive or optical connector in the dispenser housing allows periodic scanning of the sensor sheet circuitry by the control circuitry in the dispenser housing without adding connector components to the low cost, disposable sensor sheet. When a medication is ejected through the backing layer of the standard blister package, an electrical or optical parameter associated with a corresponding region of the sensor sheet is altered, thereby permitting the control circuitry to monitor the dispensing event. Stored patient compliance data may then be reported remotely through an optical or electrical interface between the dispenser and an external system for review by the pharmacist/physician.

49 Claims, 5 Drawing Sheets

ARTICLE DISPENSER FOR MONITORING DISPENSING TIMES

FIELD OF THE INVENTION

This invention relates to dispensers having detection means for sensing dispensing events, and more particularly, to a medication dispenser that can more accurately measure a patient's compliance to the prescribed dosing regimen and more accurately prompt administration of the drug based upon the measured compliance.

BACKGROUND OF THE INVENTION

A medication dispenser with compliance monitoring capability should optimally offer both single dose accuracy and accommodation of standard (as currently marketed) medication packaging. Previous designs typically either adopt a standard medication package and forsake monitoring single dose dispensing or they implement non-standard medication storage and more complicated mechanisms to provide single dose monitoring and/or single dose access control.

Pill bottle caps, as represented by the device disclosed in U.S. Pat. No. 4,939,705 of Hamilton et al. function with standard bottle packaging but allow access to the bulk medication supply during each dispensing event. Once the device recognizes the removal of the cap, any number of doses may be removed from the bottle without proper recognition, thus seriously compromising the device's ability to properly record the dosing intervals. Even more troublesome is the possibility that the cap device might not be reinstalled on the bottle; if not, then subsequent removals of medication from the bottle go unmonitored.

Dispensers described in U.S. Pat. No. 4,717,042 of McLaughlin and U.S. Pat. No. 4,572,403 of Benaroya are representative of the more complicated devices that address the issue of single dose control by requiring that the medication be placed in non-standard cellular structures and use electromechanical devices in order to control access to and monitor dispensing of a single dose of medication. The significant extra device cost due to the use of solenoids, motors, and the like, and the labor cost incurred in having to have a pharmacist or caregiver load the custom container is a serious disadvantage in an increasingly cost sensitive marketplace such as healthcare. The special loading required by this class of devices also represents additional potential for dosing errors.

The monitoring devices disclosed in U.S. Pat. No. 4,971,221 of Urquhart et al. and in U.S. Pat. No. 4,616,316 of Hanpeter et al. address the need for using more standard packaging and single dose monitoring but suffer from other disadvantages. The device of Urquhart et al. can be built around a standard blister package and monitors ejection of a medication from the package with a photo-interrupter. Because the optical sensing system must be energized at the instant the medication passes through the sensing passageway and because the sensor requires too much power for continuous battery powered operation, a dispenser access cover and opening/closing monitoring circuitry is required in order to control and conserve sensor power and to prevent false indications from objects entering the output end of the sensor passageway between true dispensing events. If the access cover is left open after dispensing a medication, the battery conservation feature is defeated, and inadvertent insertion of objects into the sensing passageway can cause dispensing data errors.

In the U.S. Pat. No. 4,616,316 device of Hanpeter et al., blister packaging technology is modified by the addition of a circuit layer to the package backing layer. As medication is pushed through the modified backing layer, a circuit is broken and a signal is communicated to the supervisory electronics through a connector attached to the circuit layer. Although this construction allows each dose removal to be monitored, standard blister packages as supplied by the pharmaceutical manufacturer are not accommodated. Rather, custom packaging with the disclosed modifications is required. Fabrication of the non-standard blister packages must include the addition of circuit layer and connector elements. Revised tooling to construct this unique package would represent a major investment and each drug so packaged would require expensive and time consuming testing for migration or leakage of foreign materials or solvents into the package. Based on these results the new package might or might not receive approval by appropriate regulatory authorities. The circuit layer and connector components add expense to what is necessarily a disposable package. Further, pharmacies would have the additional expense and inconvenience of stocking an additional presentation of the medication for use when prescribed with the dispensing device. Also, the attachment of the conductive traces directly to the backing of the medication package presents a concern whether the traces or the adhesive used to attach the traces will leach through the package and into the medication.

The Hanpeter device is intended for use in the research setting and is not appropriate for consumer use. Aligning and inserting the multi-pole connector on the modified blister package into a socket in the dispenser could represent a difficult task if performed by the patient and would contribute to installation errors during refilling and poorer reliability during operation.

It is this inadequacy of existing devices to simply and economically combine good accuracy with standard packaging, that is addressed by this invention. Use of standard packaging, as presently marketed, would make such devices more convenient and less expensive for all: patient, pharmacist, and pharmaceutical manufacturer. Uncomplicated unit dose dispensing sensitivity that conserves operating power would make such monitored dispensers more accurate, convenient to use, and economical.

SUMMARY OF THE INVENTION

The present invention is an improved dispensing monitor, particularly useful in health care, that is portable, easy to use, inexpensive, and which effectively assists a patient in following a prescribed regimen for taking medication. In addition to audible and visual prompting of dosing regimen instructions, the invention features improved methods for monitoring the release of compartmentalized, unit doses from an easily loaded cartridge stored by the device such as a unit dose card or a blister package card. The applicability of the invention to standard, marketed packaging forms, without modification, is of particular advantage. Dispensing data collected by the sensing and logic systems is available for reporting patient compliance to internal and external systems.

The medication dispenser and patient compliance monitor comprises a compact housing containing sensing and supervisory electronics, visual indicators, an audible alarm, and means to store and provide dispensing access to standard blister packaged medications. Blister package cards containing any of the common medication forms such as tablets, capsules, caplets, etc. may be accommodated by the device.

In a preferred embodiment of the invention a unique disposable sensing sheet is employed in conjunction with the standard, as-marketed blister package card to allow the logic system to sense release of each of the medications packaged in the card. The sensor sheet is a laminated assembly of two outside paper or plastic covers that support and position two interior conductive layers which overlap, and thereby make mechanical and electrical contact. One of the two exterior insulator layers has openings to allow electrical contact between the sensing circuits in the sensor sheet and a resilient, multi-pole electrical connector that is also in contact with circuits on a printed wiring board in the dispensing monitor. The dosing regimen for the particular medicine being administered can be encoded onto the blister package containing the medicine or onto the sensor sheet used with that blister package, to automatically program the device or select one of several pre-existing programs in the device. Alternatively, the dosing regimen may be programmed onto a separate programming card for use by the pharmacist or patient.

This thin, disposable sensing sheet has width and length dimensions comparable to those of the blister package card. The use of a sensor sheet with conductive traces that is separate from the blister package avoids the concern about the trace material or the adhesive used to attach the traces leaching through the package into the medication, which is present if the traces are applied directly to the package. When installed in the dispenser, the sensor sheet is in proximity to the blister package card and is so configured that a separate area of overlapping conductive traces in the sensor sheet is situated next to each compartment of the blister package. In the preferred embodiment, as a particular medication is pushed through the back of the blister package it then also passes through a corresponding conductor overlap region in the sensor sheet so that the conductive traces disengage, thereby opening the circuit associated with that one medication. Periodic scanning of the circuits in the sensor sheet by the supervisory electronics detects the change in circuit status and records in memory the date and time when that medication was released from its blister package.

The use of standard blister package cards and the connectorless design of the sensor sheet permit such easy loading of the device that the patient may refill the device without returning to the pharmacy. Loading is accomplished simply by dropping a new sensor sheet and a new blister package card into the storage cavity of the dispensing monitor. Symmetrical layout of the compartments on the blister package card and special design of the sensor sheet eliminate orientation errors. Closure of a hinged bracket locks the card of medication and the sensor sheet into the device, causes electrical connection between the sensor sheet and the dispenser electronics by compression of the resilient connector between the two circuit components, and signals to the supervisory electronics readiness to continue the dosing regimen.

Such easy, fast and error-resistant refilling permits the pharmacist to give the patient a large number of blister package cards and sensor sheets knowing that the patient or the patient's caregiver is capable of reloading the device. Substantial memory in the dispensing monitor allows the dispensing data associated with many blister package cards to be collected and stored over a long period of time. Thus the design of the present invention allows a large quantity of medication to be dispensed and monitored with a quite small and portable device without frequent visits to the pharmacy. Unlike pill bottle devices that can not be certain of how many doses were dispensed per the regimen from a bulk supply, the sensing mechanism of the present invention provides a separate signal for each unit dose dispensed. Interrogation of the patient compliance data stored by the device will detect both a taking of a dose at an improper time and a failure to dispense the medication through the device's sensing mechanism.

Medications are dispensed from the blister package card in the same manner as would be used without the dispenser. A housing plate with holes beneath each medication compartment of the blister package card provides support for easy handling of the blister package card during dispensing. In the preferred embodiment, the top of the blister package card medication compartments are exposed for easy access. While holding the dispenser in one or both hands, the patient simply pushes on the top of a blister with a thumb, forcing the medication through the foil, or foil and paper, backing layer of the blister package card and on through the circuit layers of the sensing sheet. The outer layers of the sensor sheet have been die-cut to allow easy passage of the medication through the assembly. The only extra resistance encountered by the medication passing through the sensor sheet is the force required to separate the conductive traces. This force is negligible compared to the normal force required to eject the medication through its own package.

Use of highly integrated electronic circuits and small outline surface mount packaging allows the dispensing monitor to be only slightly larger than the typical blister package card dimensions of 3 inches by 4 inches. The portable nature of the device is further enhanced by battery operation and power consumption saving designs that extend the battery changing interval to over 30 days. The long battery endurance is provided by readily available and low cost alkaline cells.

All instructions and collected patient compliance data are preserved indefinitely, even in the absence of main battery power. Patient compliance data can therefore span many thirty day battery endurance periods, up to the memory storage capacity of the electronics systems.

Dispensing data may be used by the systems internal to the dispenser and it can be ported out to other information gathering and display systems through an electrical or optical interface or by a recordable card. The compliance behavior of the patient can be examined at the end of a long course of medication or can be examined at any shorter interval as desired, without interfering with the total compliance record. Thus the dispensing data may be examined frequently, perhaps during the period associated with each individual blister package card, or it may be more convenient to take advantage of the large overall data collection capability of the device and only read out the patient compliance data at the end of the complete dosing regimen.

Accordingly, an object of the invention is to provide an improved medication dispenser with patient compliance monitoring capabilities that is small, lightweight, portable, capable of extended battery operation, rugged, economical to purchase and operate, more reliable for lack of complex and moving mechanisms, and which contains medication(s) in individual compartments, stores dosing regimen instructions for that medication(s), prompts proper patient use of the dispenser in accordance with the stored regimen, senses and stores dispensing event information, and can provide a record of the dispensing event information to an external device or system.

Another object of the invention is to provide an improved monitored medication dispenser that accommodates standard blister packaged medications in their as-marketed packages, without modifications to those standard packages such that the expense of retooling a medication package for use in the dispensing device is avoided, no new regulatory approvals of a new or altered package are required, and pharmacies are not required to stock an additional form of the same medication in order to support the dispensing aid.

It is another object of the invention to provide an improved, monitored medication dispensing device that is capable of sensing the dispensing of each unit dose or group of doses stored in the dispenser, and which provides such single dose accuracy by means of an inexpensive, disposable, connectorless, and easily oriented and loaded sensing device that is separate from the standard blister package and which is comprised of individual sensing regions that correspond to each unit dose or group of doses that are stored in the individual compartments of the blister package.

A further object of the invention is to provide a monitored medication dispensing device which allows fast and convenient loading of a blister package and dispensing sensor into the dispenser and contains sufficient memory such that a patient may be given several refill cards of a blister packaged medication along with an equal number of sensing sheets, sufficient for an extended dosing period, which the patient himself can load into the dispenser as each card is emptied through the monitored dispensing device, thereby providing the patient with a small and portable device and with the convenience of fewer trips to the pharmacy while still capturing the dispensing data for the full course of the dosing regimen for review by the pharmacist/physician.

A still further object of the invention is to provide a medication dispenser with compliance monitoring capability that employs dispensing event sensing mechanisms that require very low power such that battery endurance may be maximized and which do not have to be energized at the exact instant that the medication is removed from the device.

A further object of the invention is to provide a monitored dispensing device that is more reliable, and can permit higher article storage density, in that the article package does not have to be moved to position each article in turn in proximity to a single sensor.

Other objects, advantages, and features of the invention will become apparent from the following description taken in connection with the accompanying drawings.

DETAILED DESCRIPTION OF THE INVENTION

Figure 1:
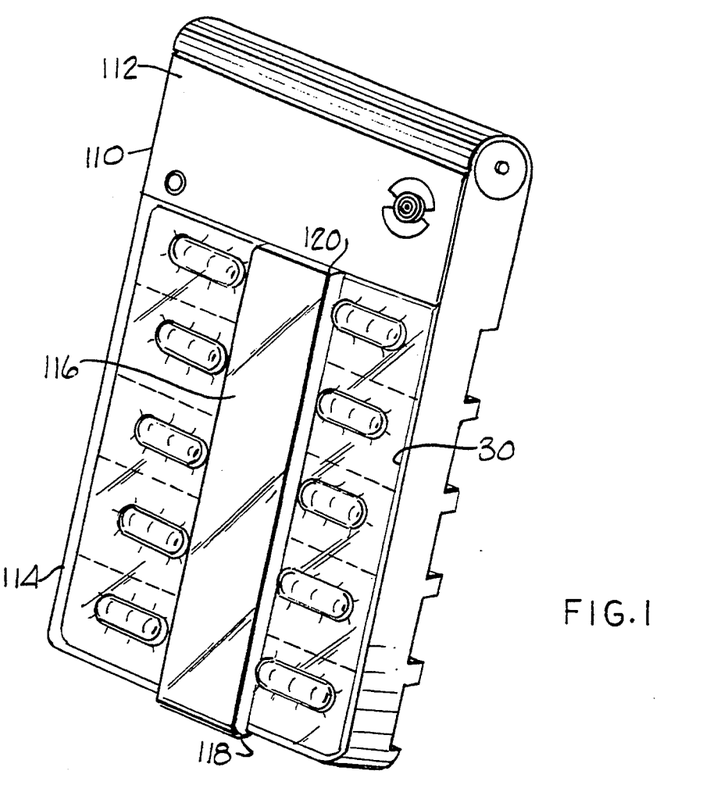
FIG. 1 is a perspective view of an assembled medication compliance monitoring and dispensing device according to the present invention.

The improved monitored medication dispenser of the present invention 110 is shown generally in FIG. 1. A preferred embodiment of the present invention permits monitored dispensing of medications presented in standard blister packages as already marketed and without modification. By accommodating an unaltered standard blister package, the need for specialized drug packaging equipment on the part of the drug manufacturer is avoided. Similarly, additional chemical and physical testing to demonstrate compatibility of the drug product with new and/or unique packaging materials or special adhesives or inks is not necessary. Further, the integrity of the standard blister package produced by the drug manufacturer is protected as a result of the minimal handling required by the invention.

Figure 2:
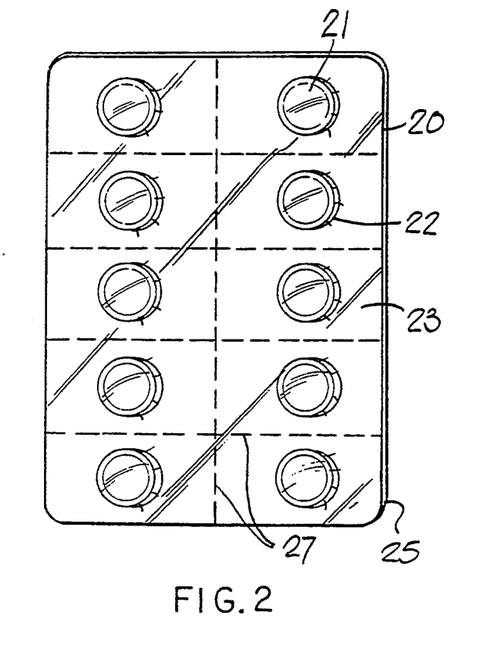
FIG. 2 is a perspective view of a commonly marketed type of card of blister packaged tablets suitable for use in the present invention.
Figure 3:
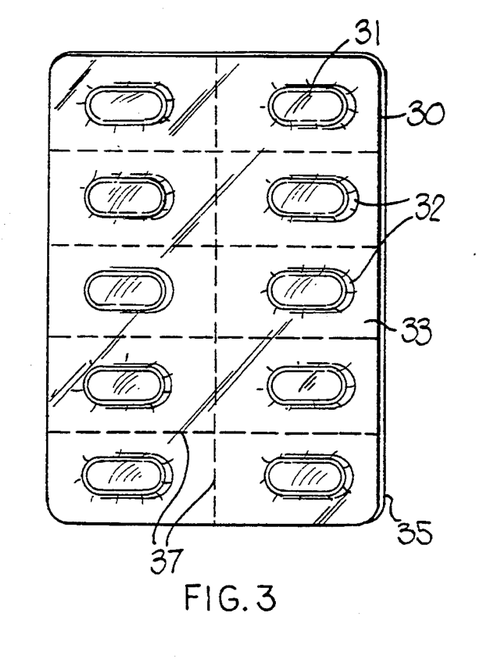
FIG. 3 is a perspective view of another commonly marketed type of card of blister packaged capsules or caplets suitable for use in the present invention.

Typical examples of cards of blister packaged medications are shown in FIGS. 2 and 3, in which FIG. 2 shows a package 20 of tablets 21 and FIG. 3 shows a package 30 of capsules or caplets 31, all of which presentations, among others, may be accommodated by the invention. The blister packs 20 and 30 are comprised of a sheet of plastic 23 and 33 in which an array of pockets or blisters 22 and 32 has been formed. The medication 21 and 31 is loaded into the blisters and a closure sheet 25 and 35, typically made of foil, is sealed with heat or adhesive to the plastic sheet thereby trapping a unit dose, or other quantity, of medication 21 and 31 in each of the blisters 22 and 32. The foil closure layer 25 and 35 may include a plastic coating (not shown) to aid heat sealing to the plastic blister sheet, and may be covered with an additional layer (not shown) to aid in childproofing the package. The blister package materials are specified such that pressure from a finger directly on a blister 22 and 32, or indirectly through some mechanical aid, will cause the medication 21 and 31 to break through the closure layer 25 and 35 and thereby exit the package 20 and 30. The individual blisters 22 and 32 are typically separated by scores 27 and 37 that allow the package to be separated into smaller packages with a fewer number of medication doses.

A card of blister packaged articles acts as a ready-made, removable, article cartridge. Cartridge packaging allows easy loading and reloading of articles into the dispenser. Loading of the cartridge into the dispenser is so fast and easy that the patient himself can readily accomplish the task. A patient can thus be given several of the blister pack cartridges in order to lengthen the interval between visits to the pharmacist. Another special advantage of using blister packaging article storage, standard or otherwise, and the disposable sensing mechanism described hereafter, is that the medication only comes in contact with its own packaging and momentarily with a disposable sensor. This effectively eliminates the potential for migration or leaching of solvents or other materials into the drug package while the package may be sitting for months or years on the pharmacy shelf. Thus, neither the medication nor the dispenser is contaminated.

Referring again to FIG. 1, the medication dispenser 110 in a preferred embodiment includes an electronic housing 112 and a medication panel 114. The blister package 30 is positioned on the medication panel 114 and is held in place by a retainer bracket 116 which is attached to the dispenser 110 by a hinge 118 on one end and a latch 120 on the other end. The medication dispenser 110 with the retainer bracket 116 and blister package 30 removed is shown from the front in FIG. 4 and from the back and side in FIGS. 5 and 5A. The medication panel 114 is a substantially flat panel having a set of holes 122 which are positioned to underlie the capsules 31 so that the capsules can be passed therethrough. The holes 122 in the preferred embodiment are bounded on the back of the panel 114 by a supporting flange 124. The flange 124 has a recessed portion 116 adjacent each hole on the side closest to the panel edge to allow the user to slip a finger adjacent the hole to aid removal of the capsule as it is forced through the hole.

Figure 4:
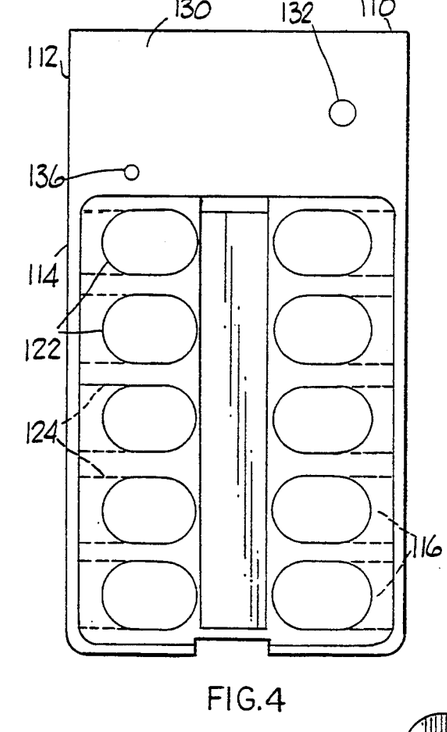
FIG. 4 is a front elevational view of the invention of FIG. 1.
Figure 5:
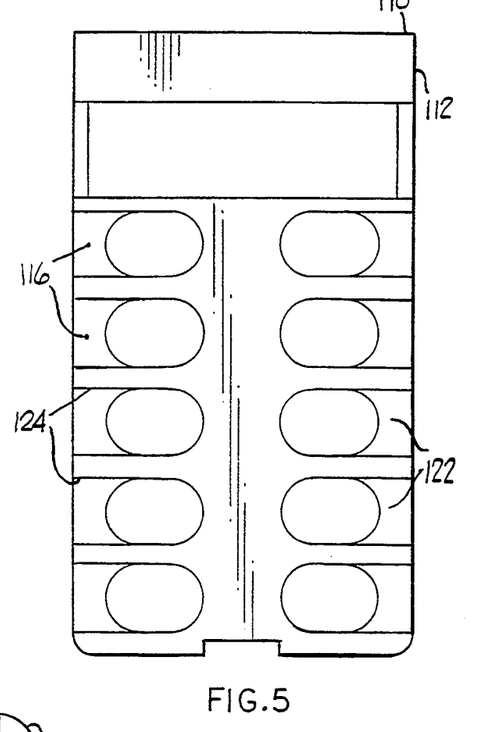
FIG. 5 is a back elevational view of the invention of FIG. 1.
Figure 5A:
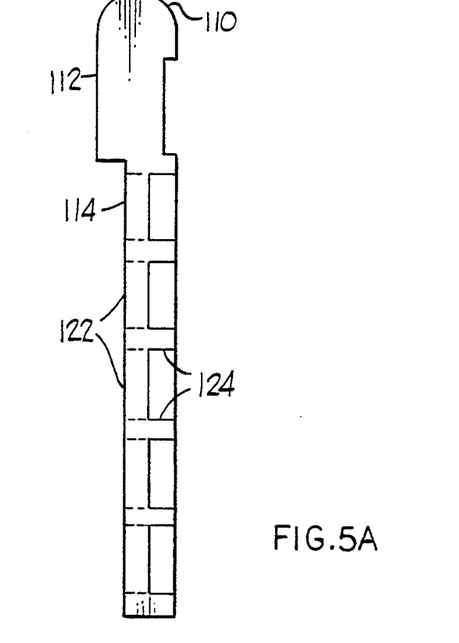
FIG. 5A is a side elevational view of the invention of FIG. 1.

The electronic housing 112 houses the electronic circuitry for the medical dispenser 110. As shown in FIGS. 1 and 4, the front panel 130 of the electronic housing includes an indicator light 132 which indicates whether it is time to administer the medication. The light may be a light-emitting diode which illuminates one color (such as red) when it is time to administer the medication, and illuminates another color (such as green) when it is not yet time to administer the medication. The front panel 130 may also include a low battery light 136 which is illuminated when the battery power is low in order to alert the user to replace or recharge the battery. If desired, the indicator light and low battery light may be illuminated intermittently in order to conserve the battery.

Next described is the sensor array to sense the dispensing of medication from the medication dispenser. In order to sense the passage of medications as they are pushed out of their blister package compartments, a sensor array has been devised which is positioned in proximity to the blister package such that the action of ejecting a medication through the closure layer of its compartment will cause a change in a sensed parameter established by a particular region of the sensing array and associated with that particular medication compartment. This sensor array may be constructed in any manner such as to create stable sensing regions associated with each article compartment and that produces a perceptible change of state of the sensed parameter when an article is dispensed from its compartment.

The parameter change associated with the dispensing of an article is normally permanent or at least long-lasting, allowing the dispensing detection circuitry to recognize the dispensing event as it occurs or at some later time after the actual instant of dispensing. This feature of the sensing array component permits periodic, rather than continuous, activation of the complete detection system, thereby contributing to lower power consumption. Scanning of the sensing array is performed at a high enough frequency that dispensing events are quickly recognized so any feedback to the patient is timely, and so that an inadvertent, subsequent status change of the sensed parameter does not mask a dispensing event.

Any electrical parameter such as current, voltage, resistance, frequency, inductance or capacitance can be used as the sensed variable. Because only two conditions of a sensing region, undisturbed, and altered by the passage of the dispensed article, are normally of interest, only two distinct values of the sensed parameter are required, thereby reducing the necessary complexity of the sensor array and the resolution capability of its associated scanning circuitry. Optical parameters such as optical intensity, frequency, and wavelength can also be used as sensor array variables, especially since low cost, plastic fiber optics can be used to form the preferred, thin, sensor array structure that can modulate optical flux parameters. In the case of either electrical or optical sensing circuitry, power consumption can be kept low by use of low-power circuit elements and, especially, by use of low duty cycle activation cycles that take advantage of the semi-permanent nature of the sensing parameter changes upon dispensing.

Another desirable feature of the sensor array is that the connection of the sensor array to the remainder of the dispensing detection circuitry in the dispensing device is made without the addition of any components to the sensor array beyond those necessary to create the sensing regions themselves. Thus, in the case of a sensor array based upon electrical parameter sensing, contact is made directly to the traces making up the sensing circuits in the sensor array without other connector means being part of the sensor array construction. Likewise an optical sensing array can be made so that optical flux is transferred directly between the scanning circuitry in the dispenser and the sensor array optical paths without the need for optical circuit termination and connector components on the sensor array that are not already inherently part of the sensing array construction. In this manner the cost of the sensor array, which usually is disposable, may be kept very low by the simplicity of the sensing array construction itself and by the absence of terminating or connecting components. The simplicity of the sensor array and its automatic connection into the dispenser's detection circuitry is also a major advantage in loading and use of this monitored dispensing device by the patient.

The sensor arrays described above, by providing a very low cost sensor for each article in the article package, eliminate the requirement to rotate or otherwise move the article package so as to position each article in proximity to a single dispensing sensor, as is commonly found in many prior art devices. The rectangular blister packages supported by the invention provide better storage density than the circular packages required in many of those rotating package, single sensor designs. Elimination of moving components also improves reliability.

In a preferred embodiment of the device, the sensor array is a disposable sensor sheet 148 and is comprised of a thin lamination of conductive and non-conductive layers that provides normally-closed switch-like structures adjacent each blister of the blister package and overlying each hole 122 of the medication panel 114. When a medication is pushed out of its compartment in the blister package, it not only penetrates the backing layer of its own package, but it also breaks through the sensor sheet 148 in one of the sensing regions where overlapping metallic foil layers have created a normally-closed switch. Only the one switch adjacent the dispensed medication is opened, thereby changing the state of only the sensing circuit associated with the particular medication that was dispensed. During the next scan of the sensing sheet by the detection circuitry in the dispenser, the status change of the particular switch is detected and the information that a particular medication has been dispensed and when it was dispensed is recorded in the dispenser's memory. A typical sensor array scanning rate of four times per second allows the detection circuitry to sense the dispensing event even if the foil layers snap back into a closed circuit condition after the passage of the dispensed medication. Subsequent open circuit signals from that sensing position are ignored until a fresh article package and sensing sheet are next loaded, thus preventing any potential false dispensing signals. Upon loading a new blister package and sensor sheet into the dispenser, the dispenser circuitry checks for a complete sensing circuit in each of the sensing regions of the sensor array sheet.

Figure 6:
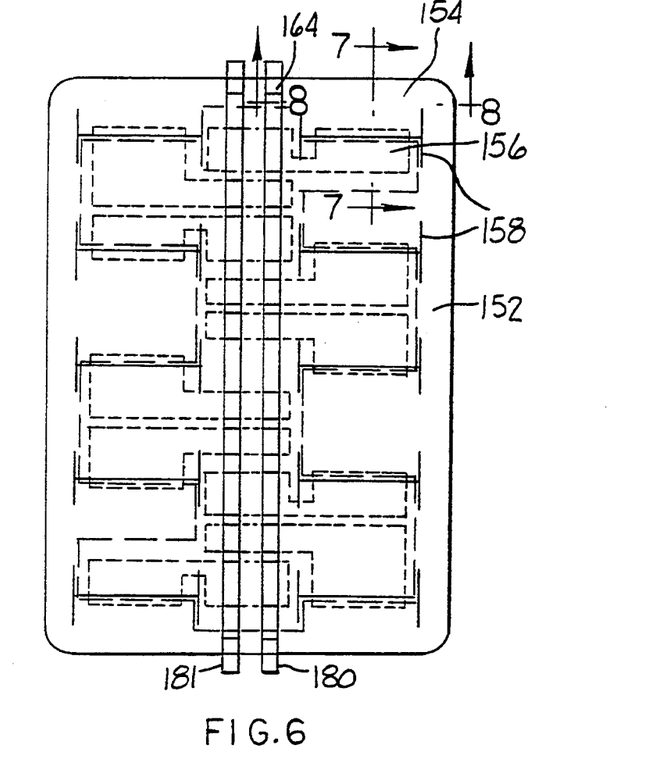
FIG. 6 is a front elevational view of the sensor array of the invention showing the layers which comprise the sensor sheet component.
Figure 7:
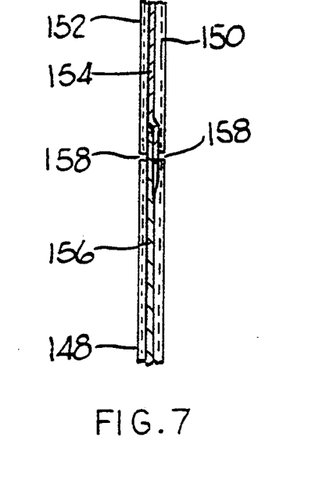
FIG. 7 is cross-sectional view of the sensor array of the invention taken along line 7—7 of FIG. 6.
Figure 7A:
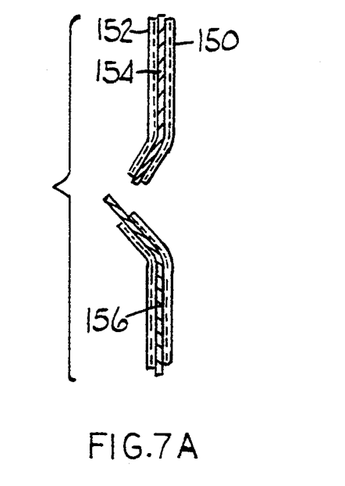
FIG. 7A is a cross-sectional view of the sensor array of the invention after dispensing medication therethrough.
Figure 8:
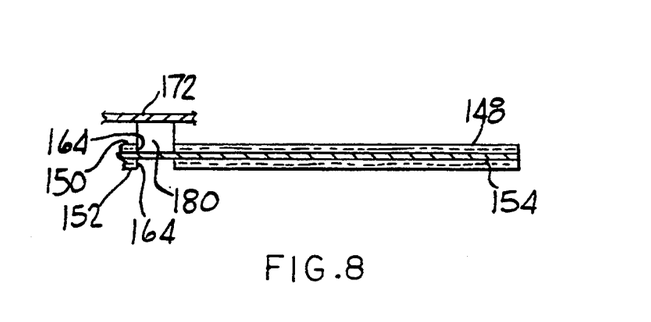
FIG. 8 is a side elevational view of the sensor array taken along line 8—8 of FIG. 6.

FIGS. 6-8 show the sensor sheet 148 of the preferred embodiment, which has non-conductive outer layers 150 and 152 and two conductive, metallic foil, circuit layers 154 and 156 therebetween. The circuit layer 154 provides a common return or supply circuit for all of the sensing paths in the sensor sheet. The signal circuit elements 156 overlap the common circuit layer at each of the article compartment areas, thereby creating simple normally-closed switch structures at each of the sensing regions. Openings 164 in the outer layers 150 and 152 allow all the signal circuits and the common circuit to be contacted by electrical connection means in the dispenser as described below. The number and position of these openings in the outer layers 150 and 152, and the symmetrical layout of the signal and common circuits around the sensor sheet longitudinal midline allow contact to be made to the circuitry in the dispenser regardless of sensor sheet 148 orientation in the medication panel 114. The sensor sheet 148 may be right side up, upside down, or turned around, and all the required electrical connections will still be made. The two outer layers may also have slits 158 in the area of the sensing region so as to reduce the force required to push a medication through the sensor sheet 148.

Figure 9:
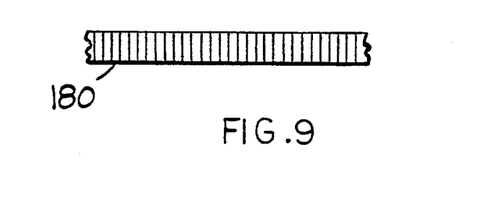
FIG. 9 is a cross-sectional view of the elastomeric connector of the invention.

Electrical connection between the sensor sheet 148 and the rest of the detection circuitry in the preferred embodiment is made by means of elastomeric connector 180. As shown in the side elevational sectional view of FIG. 9, the elastomeric connector is constructed of alternating non-conductive and conductive elastomeric layers, such as alternating layers of silicone rubber and carbon impregnated silicone rubber. Silver may also be used as a conductive filler material to make a conductive silicone rubber layer that has a lower resistance than carbon impregnated silicone rubber. The layers are in parallel planes perpendicular to the longitudinal axis of the elastomeric connector 180. The width and spacing of the conductive and non-conductive layers in the elastomeric connector strip are selected so that at least one non-conductive layer separates adjoining circuits on the printed wiring board and the sensor sheet to prevent short circuits. One or more conductive layers of the connector are in contact with traces on the sensor sheet and corresponding traces 172 on an underlying printed wiring board which are in appropriate electrical communication with the circuitry in the electronic housing 112. Thus, some of the conductive portions of the connector make electrical contact between associated circuits of the sensor sheet 148 and the underlying printed wiring board, thereby accomplishing multiple electrical connections by means of one low cost component. Because the elastomeric connector only requires surface contact with the traces on the sensor sheet 140, no expense-adding connector or terminating components are needed on the sensor sheet. Only a light compressive force, provided by the retainer bracket 116, is required to complete the electrical connection between the elastomeric connector conductive layers and the conductive traces with which it is in contact. A switch (not shown) may be used to signal proper closure of the retainer bracket 116 and can be used to alert the supervisory electronics that a refill operation has been completed. The resilient nature of the elastomeric connector and the constant compression force on it produce a reliable electrical connection that is resistant to vibration and corrosion. As shown in FIG. 6, there may also be a redundant elastomeric connection 181 to ensure good electrical connections and to assist in mechanically securing the blister package 30 in place.

In the preferred embodiment a sensor sheet 148 fabricated as described above and designed for use with the particular geometry of article compartment blisters 31 in the package to be dispensed is first placed onto the medication panel 114. As explained above, the sensor sheet may be so constructed that proper connection is made to the scanning circuitry regardless of the orientation of the sensor sheet, thereby simplifying use and eliminating potential patient loading errors. A blister package 30 of the proper type is then placed over the sensor sheet 148 with the blister package backing layer adjacent the sensor sheet. Retainer bracket 116 is closed and latched to retain both the blister card 30 and the sensor sheet 148 in the dispenser and to cause a compressive force to be exerted upon the blister card 30, sensor sheet 148, elastomeric connector 180, and underlying printed wiring board with its corresponding terminals 172. This compressive force causes the elastomeric connector 180 to make electrical connection between the sensor sheet 148 and the corresponding terminals 172 on the printed wiring board, thus completing the detection circuits and readying the device for monitoring dispensing actions.

It will be appreciated that the sensor sheet could be placed over rather than under the blister packaging. In that embodiment, the user would depress a key of an overlying keyboard or otherwise pierce the conductive traces on the sensor sheet overlying the blister package in order to press the medication tablets through the blister package bottom. As in the main embodiment, this alternative embodiment would allow use with standard as-marketed blister packaging.

When a medication is dispensed by the patient from the blister package 30, the corresponding sensor sheet 148 sensing region is altered, and the next scan of the sensor sheet circuits by the detection circuitry will indicate that a particular medication has been dispensed. The scanning frequency can be any rate that suits the desired dispensing time resolution and battery endurance considerations. A scanning frequency of 4 scans/second gives fine dispensing time resolution, allows responsive feedback to the patient, and is reasonable in terms of practical power constraints. Visual indicators and audible alarms may be incorporated in the dispenser to prompt the patient when to dispense a medication from the dispenser. Dispensing data, including date and time of dispensing, and the particular article that was dispensed, may be stored in the device memory for immediate or later, internal or external use. Since the sensing circuitry is designed to detect the dispensing of every individual article in the compartmentalized package, an accurate record is available as to when each dose was dispensed, unlike the situation with bottle cap or other bulk dispensers that do not sense removal of individual doses. A pharmacist, physician, or other caregiver can thus make informed decisions regarding the patient's regimen compliance with confidence that can only come from knowing the dispensing time for every individual dose in the package.

Because the loading of blister packages 30 into the device can be easily accomplished by the patient, the pharmacist can give the patient several of the blister package cards to use over an extended dosing period. The patient and the pharmacist/physician understand that the proper use of the dispenser and the level of compliance to the dosing regimen for all of the provided doses will be demonstrated by the record in the device memory which can span the time period for the total number of doses on all of the blister packages.

Figure 10:
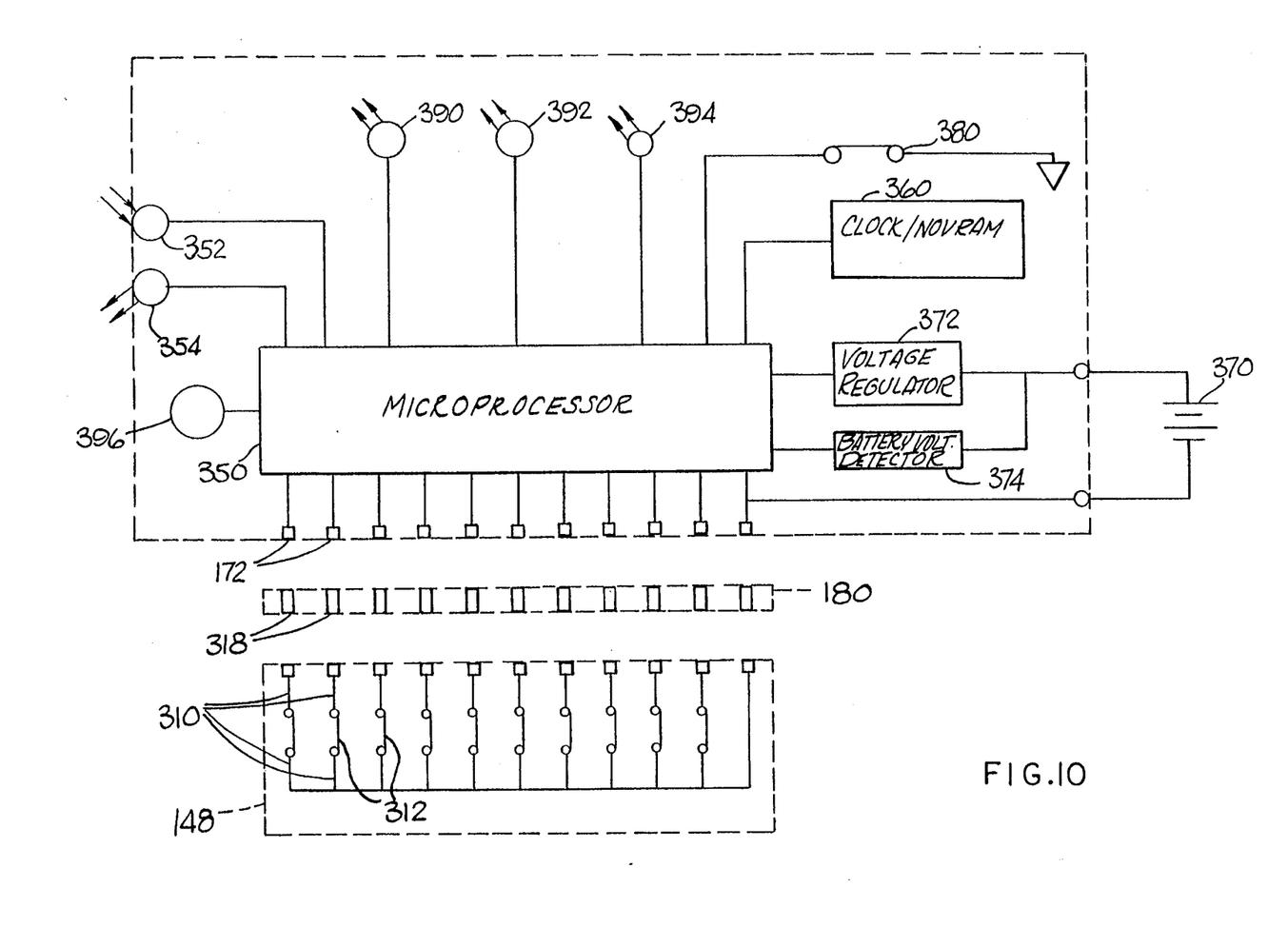
FIG. 10 is a block diagram of the electrical system of the invention.

A diagram of the electrical system of the dispenser 10 is shown in FIG. 10. The system includes the set of overlapping traces 310 of the sensor sheet 148 which form a set of normally closed switches 312. The sensor sheet 148 engages the elastomeric connector 180 in order to establish electrical connection with the terminals 172 on the underlying printed wiring board through the electrical paths 318 in the alternating layers of the elastomeric connector. The terminals 172 of the printed wiring board are connected to a microprocessor 350 which includes a read-only-memory and a random-access-memory. The microprocessor may be programmed to establish a desired dosage schedule and to store in the memory the actual dispensing times of the medication. Outside communication with the microprocessor in order to program it and to download dispensing data is accomplished through communication ports 352 and 354.

The microprocessor 350 is in communication with a real time clock/NOVRAM 360 to indicate the time on a real time basis so that the time of medication dispensing can be stored in the NOVRAM memory. The electronic circuitry is powered by a battery 370 which may be rechargeable and which is regulated by a voltage regulator 372. A low battery detector 374 may be included to detect low battery power. There may be a mechanical switch 380 operable by the closure of the retainer bracket 116 to confirm loading of the blister package 30, sensor sheet 148 and closure of the retainer bracket 116.

A set of indicators 390, 392, 394 and 396 are used to communicate the dosage schedule to the user. A "take now" indicator light 390 illuminates when it is time to administer the medication according to the programmed dosage schedule. A "not due" indicator light 392 illuminates when it is not yet time to administer the medication. As mentioned above, these two indicator lights may be in a single light housing and may be distinguished by different colors. A low battery indicator light 394 illuminates when the low battery detector 374 detects low power in the battery 370. The other indicator 396 is an audible piezoalarm which sounds to indicate to the user that it is time to administer the medication according to the programed dosage schedule. The indicators may be programmable by the user or a pharmacist using programming means (such as an uploaded personal computer) or by the sensor sheet itself with suitable encoding thereon. The program may be designed to alert the patient to administer a dose every fixed time interval, and may accumulate unadministered doses or not accumulate unadministered doses depending on the characteristics of the medicine and the desires of the prescribing physician. Alternatively, the program may be designed to indicate that a dose is due a fixed time after the last dose was actually administered, so that if one dose is administered late the next dose will also be administered late to prevent too many doses being administered in too short a time.

Although the invention is particularly advantageous when providing monitoring of article dispensing from standard blister packages, many other, less standard, cellular article storage arrangements can also be accommodated. Supporting sheet openings and tabs at each article position could be constructed as to provide a friction or snap-fit retention of the articles to the supporting sheet. Such a structure maintains the advantages of a low cost, disposable, and easily loaded article cartridge, but allows articles to be loaded into the structure, manually or with the aid of machines, that may not otherwise be available in blister packages or other cellular packaging that can take advantage of the dispensing monitoring offered by the present invention. Similarly, a blister sheet without a closure layer could be used for positioning articles in a compartmentalized structure that works with the dispenser, without the need of blister package sealing equipment or closure layer materials. In this case the sensor sheet itself, adjacent the openings of the blisters, provides the means to contain the articles in their respective compartments.

If so desired the article compartments could be an integral part of the dispenser rather than a removable element. For example, compartments may be formed in the dispenser by means of a honeycomb structure wherein the sensor sheet forms the bottom wall for the compartments. A cover membrane retains the articles in the dispenser while providing flexible, button-like, plungers over each compartment that can be depressed with a finger to push an article through the sensor sheet below and out of the dispenser. Loading of such a configuration of the invention is not as fast as when using cartridge article storage means, but the arrangement allows the manual compartmentalization of articles that might otherwise only be offered in bulk supply containers that are not capable of monitoring dispensing of single articles.

The cellular nature of the dispenser and the sensing array's ability to recognize from which of several compartments an article has been dispensed provides the capability to determine what type of article has been dispensed from a dispenser that has been loaded with more than one type of article according to a positional loading plan. For example, the blister package could be loaded with two different medications, perhaps one medication in one row of five compartments and another medication in the other row of five compartments. The dispenser can include an indicator that prompts the patient from which row to dispense a medication according to which medication is next due to be taken. The sensing array detects from which of the ten compartments a medication is dispensed and records and otherwise acts upon the positional dispensing information that is known to correspond with particular medications. Any desired allocation of a particular article to a particular set of cells may be chosen. The prompting means can then guide the patient to dispense the various medications in any sequence as desired, unlike other dispensers that require that multiple medications be taken in a fixed sequence that cannot easily accommodate occasional noncompliance by the patient to the desired sequential regimen.

The simplest method of releasing articles from the compartmentalized structures described above is to push directly with a finger upon the yieldable structure covering the article. It will also be apparent to those skilled in the art that a mechanical system could be employed to transfer or leverage finger pressure to the yieldable structure covering the article.

In the preferred embodiment the sensed parameter of the sensing array is electrical current flowing through switches beneath each blister of the blister package. When a medication passes through the sensing sheet while being dispensed it forces open the overlapping foil electrical contacts forming the switch, thereby breaking the current path through that sensing region. The presence or absence of that sensing current causes a voltage drop across a resistor in another section of the detection circuitry so as to create a signal that can be detected by the device's microprocessor.

Other electrical parameters could also be incorporated as the sensor array variable that is altered by a dispensing operation and its state sensed by circuitry in the dispenser. Foil traces in each sensing region could be positioned to develop a particular electrical capacitance, rather than a normally-closed switch, at each sensing region. A medication penetrating or otherwise deforming the capacitance structure would alter the capacitance value of the circuit and could be detected as a change in the frequency of a scanning signal applied to the particular sensing circuit. Similarly, various conductive element patterns could be used to create a resistance or inductance value that is changed by dispensing an article in proximity to the sensing region and sensed as a changing voltage, frequency, or other electrical value by the detection circuitry.

Although they may require more complicated detection circuitry, analog schemes are also possible, rather than the binary designs discussed to this point. The analog value of each sensing region variable may be measured independently, or the resistive, capacitive, or other sensing region elements may be connected in series or parallel so that each dispensed article causes a change in the overall sensing value of the sensor array as a whole. Changes in a series or parallel connected array of sensor elements would signal how many, but not which, articles had been dispensed. Such analog sensing arrays would require only two circuit connections to the dispenser electronics rather than the many circuit connections required by a sensor array of non-interconnected sensing regions.

A sensor array based upon an electrical sensing parameter can be fabricated from a number of material and process alternatives. As described above, die-cut metallic foil circuit layers laminated onto one or more die-cut supporting substrate layers can provide a low cost, disposable sensor array capable of establishing sensing regions based upon any of several electrical parameters. The conductive circuits of the sensor sheet could also be comprised of conductive inks or adhesives that have been silk-screened, or otherwise applied, to an insulating substrate. Depending on the construction of the sensor array and the associated foil, it may be possible to prevent dispensed medications from re-entering the blister package, so that the sensor array effectively acts as a one-way dispensing gate. Alternatively, the sensor array may include a separate structure for accomplishing the one-way gates. A single metallic foil layer which is perforated across the traces in each sensing region could replace the two overlapping foil layers described above. Pushing a medication through the sensor sheet would break the sensing circuit at the perforation. This perforated foil design and the conductive ink/adhesive designs have the advantage of requiring only a single conductive layer, but would require more force to push the medication through the sensing layer.

The conductive material should be nonoxidizing and physically stable enough to provide reliable contact surfaces on each of the sensing region circuits for interfacing to the elastomeric or other connector element. The materials and construction of the sensing array must also allow the physical change of a sensing region to occur with a reasonable application of force provided by the dispensing operation. Overlapping metal foil circuit elements are particular advantageous because they provide a switch condition that is resistant to normal environmental conditions such as impacts and vibration, but require only a modest force to slip past one another when a medication is pushed through the structure. Printed conductive ink or adhesive traces that must be broken to signal a state change would need to be of a thickness that allows fracture during dispensing without inadvertent cracking or rupture during normal handling. Special conductive inks and adhesives that are formulated to provide a higher degree of flexibility would be the natural choice for this application.

Figure 11A:
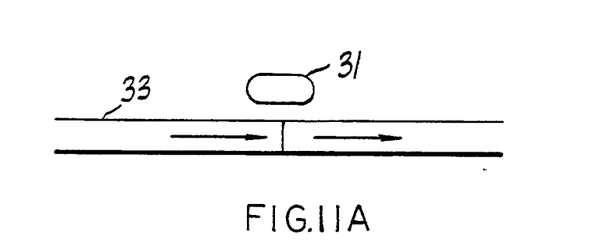
FIGS. 11A and 11B show a closed and open, respectively, optical circuit for use with the invention.

A sensor array can also be constructed of optical structures and meet the objectives of the invention. Small diameter, plastic optic fibers may conduct light to form optical circuit paths equivalent to the electrical circuit paths of the preferred embodiment described above. At each sensing region two optic fiber ends abut one another so that light is transferred from one optic fiber to the other optic fiber, forming a normally closed optical switch as shown in FIG. 11A in which the optical circuit 33 is closed and FIG. 11B in which the optical circuit 33 has been opened by the passage of a capsule 31. One end of each optical circuit in the sensing array receives light from a light flux emitter in the dispenser. The other end of each optical circuit is aligned with a light flux sensing means in the dispenser that is associated with the corresponding sensing region of the sensor array and its associated article compartment.

Figure 11B:
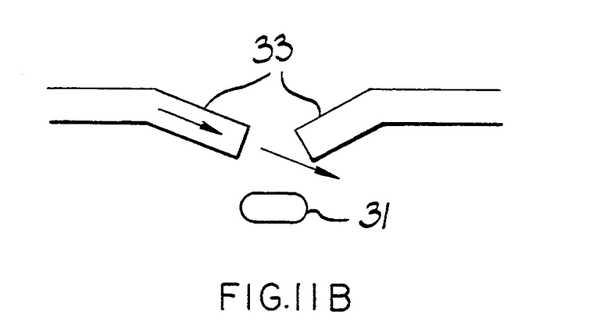

When a medication is dispensed, it penetrates a sensing region of the sensing array and causes the abutting optical fiber ends in that region to separate and thus interrupt transmission of light through the one optical switch and its associated optical circuit. Periodic activation of the sensing array by injecting light into the sensing circuits and scanning the series of light detectors that receive light from undisturbed optical circuits in the array allow the status of the sensing regions and their corresponding articles to be determined. It should be noted that the optical sensing array, like the electrical sensing arrays described above, require no connector components in the array structure. Light may be injected into and received from the optical sensing array merely by positioning the array such that the communicating ends of the optic circuit fibers are in proximity to optical or electro-optical transmitting and sensing elements in the dispenser. The sensing array requires no optical connectors or special termination components.

Like its electrical counterpart, an optical sensing array can be designed to alter parameters other than flux amplitude. Use of various filters, prisms, and other wavelength sensitive optical components can create a sensing array that modulates optical wavelengths or frequencies in response to passage of a medication through or in proximity to the optical sensor array.

The sensor array need not necessarily be penetrated by the exiting medication, nor must the sensor array always be located in the path of the medications as they are dispensed. Local folding or other lesser deformation of a sensor array sensing region that is associated with a medication being dispensed can also be made sufficient to cause the necessary change in the sensing parameter. Such other arrangements allow the sensor array to be positioned in orientations with respect to the article storage compartments other than below the storage means in the path of the dispensed articles. For example, a flexible sensor sheet could be placed above a card of blister packaged articles. Sufficient finger pressure on a particular sensing region of the sensor sheet above an associated article compartment would cause deformation of the sensing region thereby changing the sensing parameter, and the same force, being coupled to the blister package by direct contact, would eject the article from the bottom of its package.

A particular advantage of the preferred embodiment is that standard blister packaged medications may be used without modification, either by the pharmaceutical manufacturer or the pharmacist. Appropriate sensor sheets are provided with the supply of blister package cards and both a separate sensor sheet and a blister package are simply loaded into the dispenser to enable monitored dispensing. Symmetry and special construction of the sensor sheet eliminate orientation concerns during loading.

A further simplification of the device loading process can be accomplished by supplying the article storage means, e.g. a blister package card, with the sensor array attached in its proper orientation by either the pharmacist or the manufacturer. Device loading is then reduced to simply loading the article package/sensor array combination into the storage cavity. Symmetry of the sensor array contact areas again eliminates most article package/sensor array orientation requirements.

The attachment of the sensor array to the article package can be accomplished by very simple means such as staking, snap-on, or low tack adhesive connection means that require only very simple, low cost, equipment, either as a last stage of manufacture or as a later assembly operation in the pharmacy, or even at the point of use. It is important to note that this post manufacture attachment operation still allows the manufacturing tooling for the basic article package to remain unchanged.

A sensor array of the configuration shown in the preferred embodiment is thin and flexible. The flexibility of the paper or plastic outer layers and the ductility of the thin metallic foil comprising the conductive traces allows the sensor sheet to be formed into non-planar shapes that permit a wide flexibility in the design of the complete dispenser. For example, the dispenser could be folded in order to accommodate twice the capacity of articles in the same length and width dimensions.

One sensor sheet with sensing regions sufficient for both blister cards spans the length of both blister cards but, because of its flexibility, can be folded when the two dispenser halves are closed. Not only are two blister cards accommodated with one sensor sheet in this method, but the traces of the folding sensor sheet also act as a flexible connector or circuit card that allows one set of detection electronics in one half of the dispenser to communicate with the sensing regions in both halves of the dispenser.

Sensor sheet flexibility can also be useful in conforming to a curved or otherwise non-planar article storage means.

Typically the sensor array is a very low cost disposable component. A disposable sensor sheet allows the dispenser itself to remain free of contamination even over long periods of use. However, the invention will also accommodate a sensor array that is a permanent or semi-permanent component of the dispenser. The deformable nature of the sensor array sensing regions can be made reversible such that the sensing regions can be "reset" when a new article package is loaded into the dispenser. Logic means in the dispenser can be programmed to ignore subsequent inadvertent status changes of an already actuated sensing region other than after a fresh article package has been loaded and all sensing regions have been reset.

In addition, the sensor array can include an encoding of the desired dosing regimen by use of a magnetic strip, a bar code or other appropriate means which are readable by an appropriate reader in the device. In that manner, the sensor array programs the device.

An elastomeric connector as described above is a particularly effective component for making the connections between the sensor array and the electronics circuitry built into the dispenser. Multiple electrical connections are made with one low cost component. Contact between the elastomeric connector and traces or pads in the sensor sheet and on the printed circuit board is maintained even in the presence of vibration or impact because of the compressive force upon the connection assembly. Because the elastomeric connector acts like a gasket, the connections are sealed from corrosive environments. Special advantages of the elastomeric connector in this application include: high reliability in difficult environments seen by a portable, consumer product; very compact, space saving; no insertion forces; and easy, automatic alignment of connections provided by the cavity that holds the sensor sheet. Because the elastomeric connector is a flexible strip, it can be positioned in a circular, oval, square, rectangular or other compact shape in order to provide a smaller connector configuration. Sensor sheet conductive traces could then be laid out as spokes from a hub to align with the conductor connection locations of the elastomeric connector polygonal shape.

Other more conventional electrical connection means can be used in the invention. Metallic leaf springs, spring loaded pins, and pins into spring fingers are some alternatives. The connector means and the sensor array may even be combined into one component. An elastomeric sensor sheet with conductive layers forming the sensing regions and other conductive layers forming a built-in elastomeric connector could thus combine both functions into one part.

The monitored dispenser design of this invention is scalable to any desired capacity of articles. Dispensers that are intended to be portable necessarily must limit the size and number of article packages stored at one time in the dispenser, but dispensers that need not be mobile could store much larger article packages. The design of the sensor array and connector means is readily extendable to accommodate any size article package.

The folded two sided storage configuration is particularly useful for increasing the capacity of a portable dispenser. This folded dispenser can use two sensor sheets, one for each of the two blister packages, or one larger sensor sheet can be folded to serve both article packages. A larger article package could also be used and itself folded to fit the smaller dispenser size.

Because the article packages and sensor sheets are so easily loaded, and because the memory means can have sufficient capacity to store dispensing data for several blister packages, almost unlimited capacity can be addressed by this invention. The patient may be given a large number of removable article packages and sensor sheets to load sequentially into the dispenser as articles are consumed. Thus, the patient is freed from frequent visits to the pharmacy for refills and carries a convenient small dispensing device, while the dispensing of a great many medications is monitored and recorded over a long dosing period.

In a complete dispensing system that incorporates the monitored dispenser of this invention, an external device may be used to communicate with the dispenser. The external device or system may be a dedicated controller intended solely for use with the dispenser or may be a general purpose device such as a computer that can be made to interface with the dispenser. In either case communication means are required in the dispenser and the external device in order for the two devices to interface with each other. The communication means could be a connector, wired port that carries serial or parallel data. Other wireless communication means are also appropriate such as optical or radio frequency links. And, as described above, the sensor sheet itself or a programming card may be used to communicate instructions to the dispenser through the elastomeric connector signal paths. A preferred embodiment of the dispenser includes a light emitting diode and photodiode components for optically communicating with a comparably equipped external device without the use of a connector.

The information passing between the dispenser and an external device could include dispensing instructions from the external controller to the dispenser. Such instructions might be loaded as the dispenser's basic operating system or might merely select a particular set of regimen parameters stored in the dispenser memory that customize the dispenser's operation for use with a particular medication, regimen, or a patient's needs or preferences.

Information flowing from the dispenser to the external device would typically include the dispensing data collected over the term of the dosing period. This dispensing data could include actual date and time of day information or simply the difference error between the desired and actual dispensing times. The dispenser might also upload data to the external device that identifies the particular dispenser and confirms the operating parameters with which it had previously been loaded.

The external device or system can then display and/or print out various compliance reports based upon the dispensing information transmitted by the dispenser. The dispensing information can be presented in detail to show individual events or summarized to give a quick indication of the overall efficacy of the patient's actual dispensing behavior.

Use of the dispensing system begins with the patient being given a preloaded dispenser and a supply of blister package refills and an equal number of sensor sheets. The dispenser prompts the patient at proper dispensing times and records the actual times when medications are dispensed as sensed by the change of status of the sensing regions of the sensor array sheet. When all the medications of a particular blister package have been dispensed, an indicator on the dispenser prompts the patient to reload the device with a fresh blister package and sensor sheet. A self-check routine checks and confirms to the patient that the device has been properly refilled. The dispenser's memory circuits retain the record of all the dispensing events spanning the entire supply of blister cards.

At intervals specified by the physician, the dispenser is connected to the external monitoring system for transmission of the dispensing data collected over the intervening dosing period. Review of the retrieved dispensing data by the patient's pharmacist, physician, or other caregiver provides the means to discover when every single unit dose, from all of the sequentially installed blister packages, was dispensed. This information, which is not otherwise reliably available, allows the pharmacist to make an informed decision as to whether any lack of drug effectiveness or side effects are the result of the drug itself or of poor patient compliance to the prescribed regimen.

What is claimed is:

1. A dispensing device for dispensing articles from an article package that includes an array of article retention areas each being designed to hold at least one article therein and each being accessible for article removal, said device comprising a housing for receiving said article package; a separate sensing array having a plurality of sensing regions wherein there is at least one corresponding sensing region for at least one said article retention area, such that the removal of an article will cause a change in a sensing parameter in said corresponding sensing region, said sensing array being positionable on the housing adjacent the article package; and detection means for determining said sensing parameters in said sensing regions of said sensing array the detection means being electrically connected to the sensing array by an elastomeric electrical connector.

2. The dispensing device of claim 1, wherein the housing is adapted for receiving an article package that is a card of blister packaged medications wherein articles are sealed within a compartmentalized plastic tray by a backing layer that is affixed to said plastic tray.

3. The dispensing device of claim 1, wherein the housing is adapted for receiving an article package that is configured and mounted in the dispenser such that the articles may be pushed directly by a finger out of the dispenser.

4. The dispensing device of claim 1, further comprising retainer means engaged with the housing for removably retaining the article package in the housing.

5. The dispensing device of claim 4, wherein said housing includes a panel, and said retainer means includes a bracket hingedly attached to said panel, the panel and bracket being adapted for removably receiving the article package therebetween.

6. The dispensing device of claim 4, further comprising sensing means operatively associated with said retainer means, for sensing whether the article package is retained by the retainer means.

7. The dispensing means of claim 6, wherein the sensing means is a switch operable by the retainer means.

8. The dispensing device of claim 6, further comprising a latch operatively associated with the retaining means to prevent removal of the articles from the article package except through the dispensing device.

9. The dispensing device of claim 1, wherein said sensing array includes at least one electrical circuit, and the sensing parameters include electrical signals in the electrical circuits.

10. The dispensing device of claim 9, wherein the electrical circuits include conductive foil current paths in each sensing region wherein the foil current path is broken by the dispensing of an article through the sensing region.

11. The dispensing device of claim 10, wherein the conductive foil includes an overlapping portion in the sensing region wherein the current path is from a first foil to a second foil which overlaps the first foil so that the overlap is discontinued and the current path broken by the dispensing of an article through the sensing region.

12. The dispensing device of claim 11, wherein the first foil of each sensing region and the second foil are in electrical communication with a common electrical connector mounted in the dispensing device to make connection between the sensor array and the remainder of the detection means.

13. The dispensing device of claim 9, wherein the sensing parameters include the electrical resistance in the electrical circuits.

14. The dispensing device of claim 9, wherein the sensing parameters include the electrical voltage in the electrical circuits.

15. The dispensing device of claim 9, wherein the sensing parameters include the electrical capacitance in the electrical circuits.

16. The dispensing device of claim 9, wherein the sensing parameters include the electrical inductance in the electrical circuits.

17. The dispensing device of claim 9, wherein the electrical circuit includes conductive ink.

18. The dispensing device of claim 1, wherein the elastomeric electrical connector comprises a strip with layers of conductive material alternating with layers of non-conductive material perpendicular to the longitudinal axis of the strip so that a plurality of electrical circuits pass through different conductive layers separated by non-conductive layers.

19. A dispensing device for dispensing articles from an article package that includes an array of article retention areas each being designed to hold at least one article therein and each being accessible for article removal, said device comprising a housing for receiving said article package; a separate sensing array having a plurality of sensing regions wherein there is at least one corresponding sensing region for at least one said article retention area, such that the removal of an article will cause a change in a sensing parameter in said corresponding sensing region, said sensing array being positionable on the housing adjacent the article package; detection means for determining said sensing parameters in said sensing regions of said sensing array, the sensing array being connected to the detection means by a flexible metallic connector.

20. The dispensing device of claim 1, wherein the sensing array is attachable to the article package so that the article package and attached sensing array can be removably received by the housing.

21. The dispensing device of claim 1, wherein the sensing regions of the sensing array are destroyed by the removal of articles from the article package.

22. The dispensing device of claim 1, further comprising a programmable memory to program the time for dispensing an article from the article package.

23. The dispensing device of claim 22, further comprising an indicator to indicate that it is time to dispense an article from the article package in accordance with the programmable memory.

24. The dispensing device of claim 1, further comprising communication means for communicating between the dispensing device and a separate programmable system.

25. The dispensing device of claim 1, further comprising a memory to enter the time at which articles are dispensed from the article package.

26. A dispensing device for dispensing articles from an article package that includes an array of article retention areas each being designed to hold at least one article therein and each being accessible for article removal, said device comprising a housing for receiving said article package; a separate sensing array having a plurality of sensing regions wherein there is at least one corresponding sensing region for at least one said article retention area, and wherein said sensing array includes at least one optical circuit such that the removal of an article will cause a change in a sensing parameter in said corresponding sensing region, said sensing array being positionable on the housing adjacent the article package; and detection means for determining said sensing parameters in said sensing regions of said sensing array.

27. The dispensing device of claim 26, wherein said sensing parameter includes the optical flux intensity through said optical circuit.

28. The dispensing device of claim 26, wherein the optical circuit includes two optical fibers having free ends abutting one another to form a connection at the sensing region.

29. The dispensing device of claim 26, wherein said sensing parameter includes the optical wavelength.

30. The dispensing device of claim 26, wherein said sensing parameter includes the optical frequency.

31. The dispensing device of claim 26, wherein the dispensing device includes an optical connector to make an optical connection between the optical circuit and the detection means.

32. A dispensing device for dispensing articles, comprising a housing; an array of article retention areas within said housing each being designed to hold at least one article therein and each being accessible for article removal; a sensing array having a plurality of sensing regions wherein there is at least one corresponding sensing region for at least one said article retention area, such that the removal of an article will cause a change in a sensing parameter in said corresponding sensing region, said sensing array being positionable on the housing adjacent the article retention areas; and detection means for determining said sensing parameters in said sensing regions of said sensing array, the detection means being electrically connected to the sensing array by an elastomeric electrical connector.

33. The dispensing device of claim 32, wherein said sensing array includes at least one electrical circuit, and the sensing parameters include electrical signals in the electrical circuits.

34. The dispensing device of claim 33, wherein the electrical circuits include conductive foil current paths in each sensing region wherein the foil current path is broken by the dispensing of an article through the sensing region.

35. The dispensing device of claim 34, wherein the conductive foil includes an overlapping portion in the sensing region wherein the current path is from a first foil to a second foil which overlaps the first foil so that the overlap is discontinued and the current path broken by the dispensing of an article through the sensing region.

36. The dispensing device of claim 35, wherein the first foil of each sensing region and the second foil are in electrical communication with a common electrical connector mounted in the dispensing device to make connection between the sensor array and the remainder of the detection means.

37. The dispensing device of claim 33, wherein the sensing parameters include the electrical resistance in the electrical circuits.

38. The dispensing device of claim 33, wherein the sensing parameters include the electrical voltage in the electrical circuits.

39. The dispensing device of claim 33, wherein the sensing parameters include the electrical capacitance in the electrical circuits.

40. The dispensing device of claim 33, wherein the sensing parameters include the electrical inductance in the electrical circuits.

41. The dispensing device of claim 32, wherein the sensing regions of the sensing array are destroyed by the removal of articles from the article package.

42. The dispensing device of claim 32, further comprising a programmable memory to program the time for dispensing an article from the dispensing device.

43. The dispensing device of claim 42, further comprising an indicator to indicate that it is time to dispense an article from the dispensing device in accordance with the programmable memory.

44. The dispensing device of claim 32, further comprising communication means for communicating between the dispensing device and a separate programmable system.

45. The dispensing device of claim 32, further comprising a memory to enter the time at which articles are dispensed from the dispensing device.

46. A dispensing device for dispensing articles from an article package that includes an array of article retention areas each being designed to hold at least one article therein and each being accessible for article removal, said device comprising a housing for receiving said article package; a separate sensing array having a plurality of sensing regions and at least one electrical circuit, including conductive foil current paths in each sensing region whereby the foil current path is broken by the dispensing of an article through the sensing region, the conductive foil including an overlapping portion in the sensing region wherein the current path is from a first foil to a second foil which overlaps the first foil so that the overlap is discontinued and the current path is broken by the dispensing of an article through the sensing region, said sensing array being positionable on the housing adjacent the article package; and detection means for determining that said current path is broken.

47. The dispensing device of claim 46, wherein the first foil of each sensing region and the second foil are in electrical communication with a common electrical connector mounted in the dispensing device to make connection between the sensor array and the remainder of the detection means.

48. A dispensing device for dispensing articles from an article package that includes an array of article retention areas, each being designed to hold at least one article therein and each being accessible for article removal, said device comprising a housing for receiving said article package; a separate sensing array having a plurality of sensing regions wherein there is at least one corresponding sensing region for at least one said article retention area, such that the removal of an article will cause a change in a sensing parameter in said corresponding sensing region, said sensing array being positionable on the housing adjacent the article package; detection means for determining said sensing parameters in said sensing regions of said sensing array; and retainer means engaged with the housing for removably retaining the article package in the housing, the retainer means including associated sensing means for sensing whether the article package is retained by the retainer means.

49. The dispensing device of claim 48, wherein the sensing means is a switch operable by the retainer means.

* * * * *